Figure 1:
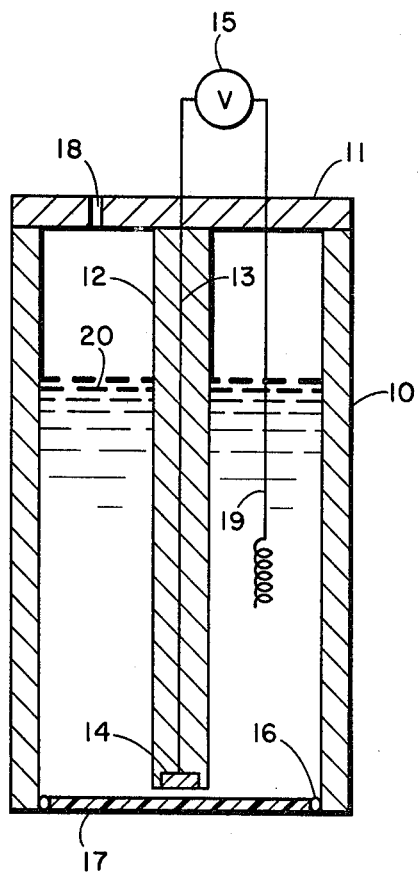

United States Patent [19]

D'Orazio et al.

[11] 4,415,666
[45] Nov. 15, 1983

[54] ENZYME ELECTRODE MEMBRANE

[75] Inventors: Paul A. D'Orazio, Mishawaka, Ind.; Arthur R. Eddy, Jr., Depew, N.Y.; Eric J. Fogt, Maple Grove, Minn.; James E. Jones, Elkhart; Bruce J. Oberhardt, Mishawaka, both of Ind.

[73] Assignee: Miles Laboratories, Inc., Elkhart, Ind.

[21] Appl. No.: 318,626

[22] Filed: Nov. 5, 1981

[51] Int. Cl.³ .................. C12N 11/12; C12N 11/04; C12M 1/40; G01N 27/26
[52] U.S. Cl. .................. 435/179; 204/403; 435/25; 435/182; 435/288
[58] Field of Search .................. 435/14, 25, 179, 180, 435/182, 288; 204/195 B

[56] References Cited

U.S. PATENT DOCUMENTS

| | | | |
|---|---|---|---|
| 3,539,455 | 11/1970 | Clark, Jr. | 435/180 X |
| 3,542,662 | 11/1970 | Hicks et al. | 435/288 X |
| 3,947,325 | 3/1976 | Dinelli et al. | 435/179 |
| 3,979,274 | 9/1976 | Newman | 435/14 X |
| 4,004,980 | 1/1977 | Emery et al. | 435/179 |
| 4,090,022 | 5/1978 | Tsao et al. | 435/179 X |
| 4,092,233 | 5/1978 | Clemens et al. | 435/14 X |
| 4,240,889 | 12/1980 | Yoda et al. | 435/288 X |
| 4,307,195 | 12/1981 | Karasawa et al. | 435/288 |

OTHER PUBLICATIONS

Kolarik et al., Glucose Isomerase Cells Entrapped in Cellulose Acetates, Immobilized Enzymes in Food and Microbial Processes, Plenam Press, N.Y., 1974, pp. 71–83).

*Primary Examiner*—David M. Naff
*Attorney, Agent, or Firm*—Roger N. Coe

[57] ABSTRACT

A membrane for electrochemical analysis is described comprising a first, relatively dense and thin layer and a second, relatively porous thick layer, which thick layer has dispersed therethrough the enzyme, glucose oxidase. The process of making the membrane by casting two to three layers of cellulose acetate compositions is also described.

14 Claims, 2 Drawing Figures

U.S. Patent  Nov. 15, 1983  4,415,666

ENZYME ELECTRODE MEMBRANE

The present relates to a membrane suitable for use with an electrochemical sensor and a method of making said novel membrane. The membranes are used in voltametric cells for electrochemical analysis commonly referred to as polarographic cells and mentioned as such hereinafter. These cells comprise an enzyme for converting a substance which is an unknown to be measured into a material which can be measured by way of an electrical signal from the cells. A wide variety of assay techniques and sensors are available for the measurement of various materials. Of particular interest to the medical field, is the measurement of small amounts of various substances contained in body fluids, such as blood, in body tissues, in foodstuffs, and the like. Such substances include glucose, urea, uric acid, triglycerides, phospholipids, creatinine, amino acids, lactic acid, xanthine, chondroitin, etc. The development of a sensor for controlling or monitoring the glucose concentration in blood or other body fluids is particularly important especially for maintaining normal blood glucose levels in a diabetic patent. Typically, blood samples are withdrawn from the patient for an on-line analysis for glucose concentrations using a glucose oxidase electrode with a polarographic detector for the generated hydrogen peroxide. Customarily, such detectors comprise an enzyme electrode for the determination for hydrogen peroxide with an anode, a cathode, an electrolyte, and a membrane of specific composition containing an enzyme that has been immobilized.

Enzymes have been used in conjunction with polarographic cells in instances where the unknown substance to be measured is not electrochemically active itself, but by conversion or reaction of the enzyme with the unknown sample, a reaction product is obtained that may be measured; that is, it is detectable by polarographic means. As stated above, the most common problem of medical interest is the desire to measure glucose in the blood. In this measurement it is advantageous to employ an enzyme to gain specificity. In the presence of the enzyme glucose oxidase the following reaction takes place:

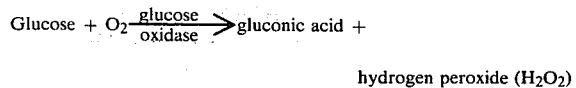

$$\text{Glucose} + O_2 \xrightarrow{\text{glucose oxidase}} \text{gluconic acid} + \text{hydrogen peroxide (H}_2\text{O}_2\text{)}$$

The hydrogen peroxide that is generated by this reaction is measurable by a polarographic detector and therefore by appropriate calibration and calculations, it is possible to determine, from the amount of $H_2O_2$ liberated, what the glucose content was in the original specimen or sample.

Generaly, a polarographic cell comprises an electrically insulating receptacle, an indicator or sensing electrode electrically contacting a membrane and a reference electrode which is electrically in contact with the membrane. By the expression "contacting" it is intended to include the situation where the contact between membrane and electrode is obtained directly or through a layer of electrolyte. Cells of various designs are widely known and understood in the art. An especially suitable cell for purposes of the invention is shown in Clemens et al, U.S. Pat. No. 4,092,233.

In the prior art, in the case of an enzyme membrane structure, it is known to arrange a second hydrophilic membrane at a distance from the first mentioned membrane. In the space between the two membranes, a layer of concentrated enzyme is present. The free face of the second membrane provides the test surface to which the substrate to be tested is applied. This type of enzyme membrane is described in the Annals of the New York Academy of Science, Vol. 102 (1962), pages 29–49. In that article, it was suggested that a pH sensitive electrode could be used to detect gluconic acid produced by the reaction. It was disclosed that the enzyme in such a system could be trapped between two cellulose acetate membranes. Glucose diffuses through the membrane and is converted by the enzyme to gluconic acid which then diffuses both towards the pH sensitive glass and back into the donor solution.

The first mentioned membrane facing the sensing electrode is made up of a material which can be penetrated by the substance to which the sensing electrode is sensitive. For example, this membrane is permeable to the reactants of the enzymatic reaction but impermeable to the enzyme itself. It may be of cuprophane but in the event that one of the reaction products is a gas at normal pressure and temperature and it is desired to measure via this gas, the membrane may consist of hydrophobic plastic impermeable to ions but slightly permeable to such gases as oxygen, carbon dioxide or ammonia. Numerous plastics having such properties are known including silicone rubber, tetrafluoroethylene and the like.

In a later type of polarographic cell developed by Clark and described in U.S. Pat. No. 3,539,455, the enzyme is placed on the electrode side of the membrane, and a platinum anode measures the hydrogen peroxide produced. Glucose, a low molecular weight species, passes through the membrane and reacts with the enzyme, but interfering high molecular weight substances such as catalase and peroxidase do not. It is disclosed that the enzymes may be held in a thin film directly between the platinum surface and the membrane by placing the enzyme on a porous film which has spaces large enough to hold enzyme molecules. However, cellophane membranes will not prevent low molecular weight interfering materials such as uric acid or ascorbic acid from reaching the sensing electrode. Clark suggests a dual electrode system to overcome that problem. The compensating electrode, without an enzyme present, gives a signal for the interfering substances while the enzyme electrode detects both the hydrogen peroxide and the interference. By calculation, the glucose level is determined. Such a dual sensor system, however, may encounter difficulties in the matching of the two cells.

It was then proposed to have an enzyme electrode which employs a thin filter membrane to prevent passage of low molecular weight interfering materials, such as uric acid and ascorbic acid, while permitting hydrogen peroxide to pass therethrough with minimum hindrance. There exist membrane materials, such as silicone rubber and cellulose acetate, which permit passage of hydrogen peroxide but which are effective barriers to interfering substances. Since this type of membrane must be placed between the sensing electrode and some component of the sensing system, it follows that in order for measurement equilibrium to be as rapid as possible, the membrane must be as thin as possible while still retaining its selectivity. In the case of a hydrogen peroxide sensing probe, this membrane will need to be less than 2 microns thick. A membrane of this thickness is difficult to use in practice because of its insufficient strength.

The art then turned to depositing the material in a thin layer on a porous substructure to provide the necessary strength while at the same time being of little hindrance to hydrogen peroxide passage, and the weak interference rejecting layer can be thin to enhance speed of response.

As described in Newman, U.S. Pat. No. 3,979,274, in a laminated two-ply membrane, an enzyme adhesive is used to bond the two-plies together. The membrane includes a support layer which controls substrate diffusion and serves as a barrier to high molecular weight substances, an enzyme preparation for reacting with the unknown and for bonding the layers together, and an essentially homogeneous layer that serves as a barrier to interfering low molecular weight materials but permits hydrogen peroxide to pass through. However in this development, it is necessary to make a sandwich consisting of two membranes with a layer of enzyme between, the enzyme acting as the adhesive or bonding agent. In this type of arrangement, the use of too much enzyme could slow down the diffusion of the diffusing species to an unacceptable amount. If a thinner layer of enzyme is used, there is acceptable diffusion, but the loading of enzyme may not be adequate.

A still later development came in British Pat. No. 1,442,303 (Radiometer) wherein there was proposed a composite membrane which is an inhomogeneous membrane formed as a unit. The membrane has two different strata, one has a thickness of less than 5 microns and the other is sufficiently thick to provide strength. The enzyme is bonded to a surface of the membrane.

Other prior art has shown a number of disadvantages. Thus, the method of Koyama et al, *Analytica Chemica Acta,* Vol. 116, pages 307-311 (1980), immobilizes glucose oxidase to a cellulose acetate membrane. This method is more time consuming; it involves more steps and suffers from the disadvantages that a monolayer of molecules would be the maximum possible enzyme load achievable.

The invention described in the present application, however, allows much greater amounts of enzyme to be spacially distributed within the membranes such that much more enzyme is available for reaction with the substrate along the diffusion path of said substrate.

Wingard et al, *The Journal of Biomedical Materials Research,* Vol. 13, pages 921-935 (1979) discloses a platinum screen or wire for immobilization of the enzyme. This would allow greater surface area to be utilized for binding than the method of Koyama et al and hence could employ greater numbers of enzyme molecules. However, the approach of Wingard is also limited to a monolayer of enzyme and capable of sustaining high conversion rates of substrate diffusing through the open spaces in the platinum screen near the surface of the platinum wire only. Hence, this prior art cannot achieve the theoretical conversion rates possible with an enzyme spacially distributed throughout a membrane through which the substrate diffuses, as is obtainable by following this invention.

In accordance with the present invention, the need to prepare a discrete enzyme layer is eliminated by incorporating the enzyme directly into one portion of the membrane in a manner whereby the enzyme is homogeneously dispersed throughout the phase of the membrane and immobilized therein.

A number of advantages characterize the present invention including ease of preparation, the permanent attachment of two phases of the membrane with no chance of separation; i.e., avoidance of lamination. Also the new membrane readily lends itself to a dip casting process whereby the membrane can be fixed directly to a miniature electrode.

In addition, a greater uniformity of enzyme concentration may be achieved by the homogeneous distribution in a membrane than by sandwiching bulk enzyme between two layers.

The principles involved in the present invention may be more fully understood with reference to the analysis of blood for glucose content. The liquid portion of blood consists of proteins, lipids, and other substances. Nonelectrolytes are present such as glucose, enzymes such as catalase, electrolytes such as ascorbic acid (vitamin C) and various metallic salts made up of cations of sodium, potassium, magnesium, calcium, iron and copper, and anions such as chlorides, phosphates, bicarbonates, and carbonates. The phosphates, carbonates and bicarbonates operate as buffers to maintain the pH of blood at a fixed level uner normal conditions. If a sample of blood were placed on one side of a membrane in a cell and an aqueous solution of the enzyme glucose oxidase and oxygen on the other side of the membrane, certain low molecular weight materials will pass from the blood through the membrane to the glucose oxidase solution. The high molecular weight materials such as the enzymes will not pass through the membrane. The rates of permeability of the various materials through the membrane are fixed because of the nature of the membrane. In this invention, the relatively thin phase has a molecular cut off of approximately 300. This means that materials of a molecular weight of greater than about 300 will not pass through.

Glucose, a low molecular weight material, will pass through the membrane and react with the enzyme glucose oxidase in the presence of oxygen to form gluconolactone and hydrogen peroxide. Gluconolactone in the presence of water will hydrolyze spontaneously to form gluconic acid.

Gluconic acid and hydrogen peroxide, being relatively low molecular weight materials compared to the enzyme glucose oxidase, will pass through the membrane. Catalase and peroxidases which are large enzyme molecules capable of rapidly destroying $H_2O_2$ and which are present in biochemical fluids are prevented from passing through the membrane.

According to the present invention, the membrane may be utilized in a cell for electrochemical analysis comprising, in general, an electrically insulating receptacle, an anode and a cathode as is shown in U.S. Pat. No. 4,092,223. The membrane of this invention may also be used in older type devices utilizing a sensing electrode (anode), a reference electrode (cathode) in a space in the receptacle which is separated from the sensing electrode and adapted to hold an electrolyte. The membrane electrically contacts the electrodes; a path for an electrical current extends between anode and cathode or between the reference electrode and the sensing electrode and the membrane comprising the two component, integrated enzyme membrane which is described herein.

One portion of the membrane of the invention has a relatively high density and is relatively thin, and the other portion of the membrane has a relatively lower density and a thicker cross-section. The portion of the membrane which has the thicker cross-section has the enzyme incorporated and immobilized therein and distributed homogeneously throughout.

It is a characteristic feature of the present invention that the composite membrane is formed in two distinct steps and had different strata or portions parallel to the surface of the membrane. If desired, however, another layer, without enzyme, may be present between the first and second layers. The use of a second phase inversion layer (without enzyme) between the dense layer and the phase inversion enzyme layer appears to allow a better membrane to be manufactured by providing more linear response characteristics. The multilayer membrane blocks the migration to the sensing electrode of interfering substances such as uric acid, ascorbic acid, and large nongaseous molecules and similar substances and allows the passing of solvent and low molecular weight species, for example, enzymatic conversion products such as hydrogen peroxide.

A membrane exhibiting these properties can be made of cellulose acetate as well as other materials such as copolymers of cellulose acetate.

It has been determined that a reasonably short measuring time requires that the thickness of the membrane should not exceed, preferably, about 70 microns although this can vary depending on the kind of measurement to be carried out. It would be possible to achieve an acceptable short response time for an equilibrium of diffusion, for example of hydrogen peroxide by designing the membrane to be made up of the thinner, more dense layer of 2 to 5 microns and the thicker, less dense layer of about 65 microns.

The weaknesses inherent in the prior art have been overcome by forming the composite membrane according to the novel method of the invention. It consists of two phases which are not necessarily distinct but which when cast separately and independently of each other are characterized as: a highly porous, relatively thick phase which in the composite membrane faces the electrodes and a relatively nonporous, denser and thinner phase which in the composite membrane faces the sample; e.g., the blood specimen. In the composite membrane, the porosities and thicknesses of the two membranes may become modified as they are fused together. This is uniformly distributed throughout the highly porous phase, a particular enzyme. This enzyme may, however, become distributed throughout the composite membrane. Since an intermingling or diffusion of the layers is believed to occur, the terms layers and phases are used interchangeably to mean layers which may interact at their interfaces.

The individual properties of the phases forming the composite membrane, if cast separately should be as follows: the relatively nonporous phase should if cast by itself and tested have a molecular weight cut off of approximately 300; the highly porous phase if cast by itself and tested should freely pass the substrate for the enzyme (at the surface adjacent to the surface onto which it has been cast) and yet exclude macromolecules such as large proteins.

In order to achieve the desired properties for detection of analyte, the membrane of the invention is fabricated in a two stage process. First, an ultra thin cellulose acetate membrane is cast or spread on a suitable surface which does not interact with or bond to the membrane. Representative surfaces to provide a support for the cast film are glass and some plastics such as polyethylene. The film is cast with conventional equipment whereby it is possible to control the thickness of the resulting film. After being spread on the surface, the cast film is dried. This thin film serves as the relatively nonporous thin phase. The thickness of this phase generally ranges from about 1 to 10 microns, preferably from 2 to 5 microns.

A thicker phase inversion type of cellulose acetate membrane containing the enzyme is then cast directly on top of the ultra thin membrane. Since both casting solutions are of the same polymer base, and preferably use the same solvent, there is a diffusion zone of the two at the interface or boundary and no clear distinction can be made between the two phases. Indeed, the order of casting may also be reversed, although it is preferred to cast the thin film first. The films may be allowed to dry under ambient conditions, or a heating device may be utilized. The first film need not be absolutely dry when the second film is cast on it; i.e., the first film may be tacky to the touch. It is believed that a skin forms on the top surface of the thick film after drying.

The solution of the cellulose acetate for the formation of the thin, more dense membrane component is formed by dissolving a cellulose acetate polymer in an inert organic solvent such as ketones. Typical are acetone, cyclohexanone, methylethylketone and the like. Mixtures of miscible solvents may also be used. Concentration of the polymer in solvent may vary, as from 1 to 5% preferably 2 to 3%. The film is cast with any suitable film applicator such as will produce a final product film thickness of 1–10 microns, preferably 2–5 microns in thickness.

The phase inversion member; that is the relatively porous thicker portion of the composite membrane of this invention, is prepared by forming a cellulose acetate polymer in solution in an inert organic solvent such as a ketone. A nonsolvent or nonsolvent mixture for the cellulose acetate such as an ethanol and water mixture is then mixed with the cellulose acetate solvent solution. The particular nonsolvent, e.g., ethanol, is not critical and others may be used. Lower alcohols mixed with water are usually preferred for this purpose. An aqueous enzyme solution is included as part of the nonsolvent phase. The enzyme, glucose oxidase, is usually employed in an aqueous solution containing from 500 to 5000 units of the enzyme per cc of water, although this can vary as will be apparent to those skilled in the art. Typical electrochemical sensors which can be employed with the membrane of this invention include the BIOSTATOR glucose electrode of Miles Laboratories, Inc. See U.S. Pat. No. 4,092,233.

The overall thickness of the membrane of the invention can vary from about 40 to about 100 microns, but is preferably approximately 70 microns. The thinner, more dense layer ranges from about 1 to 10 microns, preferably 2 to about 5 microns and the thicker, less dense range from about 40–80 microns. Some variation in these values is permissible within the contemplation of this invention. The preferred membrane is about 70 microns in thickness, with one layer about 2 microns and another layer about 65 microns in thickness.

Figure 2:
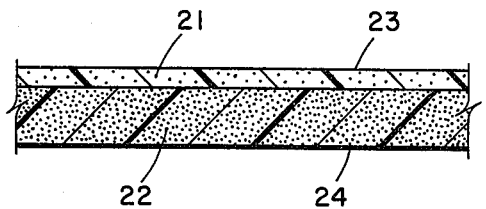

The following drawings illustrate the invention in further detail and the invention will be more fully understood by reference to these drawings wherein:

FIG. 1 is a vertical section view (partial) of a conventional polarographic cell utilizing the membrane of the present invention, and FIG. 2 is an enlarged view of a cross-section of the membrane of the present invention.

Referring to FIG. 1, there is shown a polarographic cell assembly which includes a receptacle in the form of an electrically insulating container 10 made of a plastic or glass material or any other suitable material and which may be of any cross-sectional area and shape, but is preferably cylindrical. This is covered by an electrically insulating cap 11. Positioned within the receptacle is an electrically insulating member rod, or cylindrical column 12, which contains in it an electrical conductor 13. This conductor is connected to an active or exposed element 14 which may be platinum, gold, silver, graphite or the like.

A lead is attached to the electrode which passes through the rod or column and through the cap to be connected with a D.C. voltage source 15.

The lower end of the receptacle is provided with a support means 16 such as a ring or retainer and the membrane 17 in accordance with the present invention is supported over the end of the supporting receptacle nearest the central electrode and spaced a capillary distance from the active face of the electrode. The membrane can be held in position with any suitable means, for example, by an O-ring fitting into a circular groove or other convenient means in the receptacle. A current measuring instrument (not shown) is connected in series with the cell.

Typically, the receptacle is provided with a vent 18 to permit gases to escape if pressure inside the receptacle rises to a sufficiently high degree.

An annular space is provided between the central rod and the receptacle walls and receives a reference electrode 19 which may be for example, silver chloride coated silver wire. The space 20 inbetween is at least partially and preferably completely filled with a liquid mixture of electrolyte which may be introduced into the chamber through an aperture.

In polarographic measurements, two electrodes are commonly used, one of which is polarized and does not allow current to flow until depolarized by the substance being measured. In the cell structure shown in FIG. 1, electrode 19 is the cathode and is polarized and frequently referred to as the reference electrode. The other electrode, electrode 14 as shown in FIG. 1, functions as an anode and is not polarized in the presence of the substance being measured and therefore will not restrict the flow of relatively large current and is frequently referred to as the sensor electrode. The electrodes shown in FIG. 1 are in an electrically insulating relation and the electrolyte material which occupies the chamber provides a conductive path between the two electrodes. Typical electrolytes include sodium or potassium chloride, buffers including carbonates, phosphates, bicarbonates, acetates, alkali or rare earth salts or other organic buffers or mixtures thereof may be used. The solvent for such an electrolyte may be water, glycols, glycerine and mixtures thereof as is well known in the art.

FIG. 2 shows a membrane in cross-sectional detail. The nonhomogeneous membrane has a thin, dense layer 21 and a thick, less dense or porous layer 22 which layers together form the composite structure. The enzyme shown symbolically by dots is dispersed uniformly in the thick portion or strata of the membrane. However, some of the enzyme may diffuse into the thin layer during preparation of the membrane before the solvent for the cellulose acetate has evaporated. Membrane surface 24 is in electrical contact with the electrode. The membrane comprises the nonhomogeneous combination of the two layers and the enzyme, the outer free surface of which 23 represents the test surface which is to be brought into contact with the solution to be analyzed.

In the preferred embodiment, the inner surface 24 which is an electrical contact with the electrode is about 65 microns in thickness and the opposite layer in contact with the sample to be analyzed is about 2 microns. The overall thickness of the membrane is preferably about 70 microns.

The membrane of the invention may be produced by first casting an ultra thin, relatively dense cellulose acetate membrane onto a suitable surface and permitting it to dry. If the thin layer is omitted, the measurements may be more subject to nonlinearity due to oxygen depletion which is, in turn, caused by an increased flux of glucose molecules transported through the membrane and reacting with enzyme. Then the thicker phase inversion type cellulose acetate membrane which is relatively porous may be cast directly on top of the thin membrane. It may be possible to first cast the thick portion of the membrane and then cast the thin portion directly on top of it.

The phase inversion member or more porous portion of the membrane composite is formed by providing a solution of cellulose acetate in an organic inert solvent such as acetone. The solution is then mixed with a non-solvent for the cellulose acetate. Suitable nonsolvents include ethanol and water mixtures.

It is also desirable that the aqueous enzyme solution be introduced as a part of the nonsolvent phase.

The following specific example illustrates how the invention may be carried out but should not be considered as limiting thereof in any way.

EXAMPLE

On a clean glass plate, spread a 3% cellulose acetate in acetone solution with 2 mil film applicator to prepare the first film portion.

Prepare the phase inversion cellulose acetate casting solution by mixing 1.5 cc of ethanol with 5 cc of a 10% cellulose acetate in acetone solution. This is then placed in a salt water ice bath and stirring of the solution is continued. In 0.1 cc increments, a total of 1.0 cc of an aqueous glucose oxidase solution is then added to the solution. This solution contains 2,000 to 3,000 units of the glucose oxidase per cc of solution. This is mixed for 10 to 15 minutes. The mixing is then stopped and the material is allowed to deaerate for 5 minutes.

The second membrane solution is then spread on top of the first membrane with a 18 mil applicator. The spread film is then permitted to dry for several hours at room temperature. The membrane is then ready for use.

The enzyme preparation may simply be a mixture of the appropriate enzyme such as glucose oxidase in water. Of course, other materials such as a binder or crosslinking agent like glutaraldehyde may be included in the enzyme preparation. Likewise, the proportion of enzyme to water in the preparation is immaterial as long as a flowable paste or solution is formed which may be coated or pressed easily into the solution. Sufficient enzyme is incorporated into the solution to prepare an adequate reactive amount for measurement.

The membrane composite of the present invention is a self-supporting film of a total thickness which may range from about 50 to 100 microns, preferably about 70 microns. The composite membrane may be shaped to any particular configuration or size or may be cut or dimensioned in any particular way to fit receptacles for polarographic cells or electrodes of any suitable dimension. It may, in particular, be fastened to an O-ring for use in an electrode such as described in U.S. Pat. No. 4,092,233.

To fasten the membrane to a rubbery O-ring of an appropriate size, a gluing operation may be employed. The membrane may also be cast directly onto an electrode surface.

In addition to cellulose acetate, other polymers capable of being dissolved in solvents and undergoing phase inversion with the addition of a weak solvent of nonsolvent would be potential membrane materials. Such polymers include cellulose nitrate, ethylcellulose and other cellulose derivatives. In addition, polycarbonate is a suitable alternative if methylene chloride is employed as a solvent instead of acetone or other ketones.

As a substitute or alternative for the lower alcohols present in the phase inversion mixture formamide can be used.

Further variations and modifications of the invention as will be apparent to those skilled in the art after reading the foregoing are intended to be encompassed by the claims that are appended hereto.

We claim:

1. A method of making a 40 to 100 micron contiguous multilayer membrane suitable for use with an electrochemical sensor in the measurement of an unknown which comprises:
providing a first polymer dissolved in an inert organic solvent and casting said polymer in solution onto an inert support surface which is unreactive with said polymer and does not form a bond to said polymer,
permitting said solution to form a 1 to 10 micron dense relatively nonporous film and thereby obtain a first layer,
providing a second polymer dissolved in an inert organic solvent, mixing said second polymer dissolved in solvent with a nonsolvent for said polymer and with glucose oxidase to obtain a dispersion and thereafter casting said dispersion onto said first layer, and thereafter permitting said second polymer to dry to form a second 40 to 80 micron highly porous layer less dense than the first layer,
thereby forming said contiguous multilayer membrane, said layers of the membrane being fused together such that no clear distinction can be made between the layers at the boundary and the boundary between the layers is a diffusion zone.

2. A method of making a 40 to 100 micron contiguous multilayer membrane suitable for use with an electrochemical sensor in the measurement of an unknown which comprises:
providing a first polymer dissolved in an inert organic solvent by mixing said first polymer in solution with a nonsolvent for said polymer and with glucose oxidase to obtain a dispersion,
casting said dispersion onto an inert support surface which in unreactive with said polymer and does not form a bond to said polymer,
permitting said dispersion to form a 40 to 80 micron highly porous film and thereby obtain a first layer,
providing a second polymer dissolved in an inert organic solvent,
casting said second polymer onto said first layer and permitting said second polymer to dry to form a second 1 to 10 micron relatively nonporous layer more dense than the first layer,
thereby forming said contiguous multilayer polymer membrane, said layers of the membrane being fused together such that no clear distinction can be made between the layers at the boundary and the boundary between the layers is a diffusion zone.

3. The method of claims 1 or 2 wherein the inert organic solvent reacted with said first and second polymer is the same.

4. The method of claim 3 wherein the inert organic solvent is a ketone.

5. The method of claim 3 wherein the inert organic solvent is acetone.

6. The method of claims 1 or 2 wherein the glucose oxidase is present in a mixture of water and ethanol.

7. The method of claim 1 wherein said first layer is formed from a 3% cellulose acetate in acetone and said first layer is about 2 microns in thickness.

8. The method of claim 1 wherein said second layer is formed from 10% cellulose acetate solution in acetone which is mixed with a solution containing ethanol and glucose oxidase in water or buffer.

9. The method of claim 2 wherein said first layer is formed from 10% cellulose acetate in acetone solution which is mixed with a solution containing ethanol and glucose oxidase in water or buffer.

10. The method of claim 2 wherein said second layer is formed from a 3% cellulose acetate solution in acetone and said second layer is about 2 microns in thickness.

11. The method as defined in claims 1 or 2 wherein in forming the layer containing glucose oxidase, cellulose acetate solution is mixed with glucose oxidase by mixing 1.5 cc of ethanol with 5 cc of a 10% cellulose acetate solution in acetone in a salt water ice bath with continuous stirring, the 1 cc of an aqueous glucose oxidase solution containing 2,000 to 3,000 units per cc, is added incrementally with continuing mixing for 10 to 15 minutes to the cellulose acetate solution to form a dispersion and deaerating for 5 minutes.

12. In a polarographic cell structure for use in electrochemical analysis of an unknown comprising an electrically insulating receptacle, an electrode means mounted in said receptacle, and a membrane means, the improvement which comprises utilizing the membrane defined by claims 1 or 2.

13. A membrane having a total thickness of about 40 to about 100 microns for use in a polarographic cell for the electrochemical analysis of an unknown comprising a first 1 to 10 micron dense relatively nonporous layer of essentially homogeneous cellulose acetate and a second 40 to 80 micron highly porous less dense layer of cellulose acetate separately fused to said first layer, said second layer containing glucose oxidase dispersed throughout, wherein the boundary between the two layers is a diffusion zone and no clear distinction can be made between the layers at the boundary.

14. A membrane for use in a polarographic cell for the electrochemical analysis of an unknown and which is made by the method of claims 1 or 2.

* * * * *